(12) United States Patent
Kugelmann et al.

(10) Patent No.: US 7,838,034 B2
(45) Date of Patent: Nov. 23, 2010

(54) INTRAVENOUS PHARMACEUTICAL FORM OF ADMINISTRATION

(75) Inventors: Heinrich Kugelmann, Aachen (DE); Johannes Bartholomäus, Aachen (DE)

(73) Assignee: Grunenthal GmbH, Aachen (DE)

( * ) Notice: Subject to any disclaimer, the term of this patent is extended or adjusted under 35 U.S.C. 154(b) by 0 days.

(21) Appl. No.: 11/046,631

(22) Filed: Jan. 27, 2005

(65) Prior Publication Data

US 2005/0136120 A1 Jun. 23, 2005

(30) Foreign Application Priority Data

Jul. 30, 2002 (DE) ................. 102 34 784

(51) Int. Cl.
*A61K 9/14* (2006.01)
(52) U.S. Cl. .................................... 424/489
(58) Field of Classification Search ............. 424/1
See application file for complete search history.

(56) References Cited

U.S. PATENT DOCUMENTS

| | | | | |
|---|---|---|---|---|
| 5,091,188 A | * | 2/1992 | Haynes | 424/450 |
| 5,510,118 A | | 4/1996 | Bosch et al. | 424/489 |
| 5,654,008 A | * | 8/1997 | Herbert et al. | 424/489 |
| 5,785,976 A | | 7/1998 | Westesen et al. | 424/400 |
| 6,306,366 B1 | * | 10/2001 | Heldmann et al. | 424/9.52 |
| 6,337,092 B1 | | 1/2002 | Khan et al. | 424/489 |

FOREIGN PATENT DOCUMENTS

| | | |
|---|---|---|
| DE | 36 23 376 A1 | 1/1988 |
| DE | 37 42 473 A1 | 7/1988 |
| DE | 44 40 337 A1 | 5/1996 |
| EP | 0 161 445 A1 | 11/1985 |
| EP | 0 209 403 A2 | 1/1987 |
| EP | 0 499 299 A2 | 1/1992 |
| WO | WO 91/14455 | 10/1991 |
| WO | WO 96/11669 | 4/1996 |
| WO | WO 99/00113 | 1/1999 |

OTHER PUBLICATIONS

"Acetaminophen". Dictionary.com. Online. Internet. Accessed on Jun. 21, 2005. <http://www.dictionary.reference.com/search?db=mwmed&q=acetaminophen.*
"Intravenous". Thesaurus.com. Online. Internet. Accessed on Jun. 21, 2005. <http://www.thesaurus.reference.com/search?q=intravenous.*
"Absolute Bioavailability of Paracetamol after Oral or Rectal Administration in Healthy Volunteers", M. Eandi, et al., Arzneimittel-Forschung, Drug Research, vol. 34, No. 8, Aug. 1984, pp. 903-907.
"Nanosuspensions for the formulation of poorly soluble drugs I. Preparation by a size-reduction technique", Rainer H. Muller, et al., International Journal of Pharmaceutics 160 (1998) 229-237.
"Nanosuspensions—A Novel Formulation for the I.V. Administration of Poorly Soluble Drugs", R.H. Muller, et al., Proc. $1^{st}$ World Meeting APGI/APV, Budapest, May 9/11, 1995, 491-492.
"Preparation of a clofazimine nanosuspension for intraveneous use and evaluation of its therapeutic efficacy in murine *Mycobacterium avium* infection", K. Peters, et al., Journal of Antimicrobial Chemotherapy (2000) 45, 77-83.
"Nanosuspensions as a new approach for the formulation for the poorly soluble drug tarazepide", C. Jacobs, et al., International Journal of Pharmaceutics 196 (2000) 161-164.
"Formulation and Antitumor Activity Evaluation of Nanocrystalline Suspensions of Poorly Soluble Anticancer Drugs", E. Merisko-Liversidge, et al., Pharmaceutical Research, vol. 13, No. 2, 1996, 272-278.
"Hydrosols—Alternatives for the Parenteral Application of Poorly Water Soluble Drugs", Peter Gabmann, et al., Eur. J. Pharm. Biopharm. 40 (2) 64-72 (1994).
In: Pharmacopeia European, 1997, Chap. 2.2.35, 1997 p. 38.
"Physiologie des Menschen", R.F. Schmidt, et al., Springer-Verlag, Berlin Heidelberg New York 1980, Table of contents.
"Ultrasound Doppler Measurements of Low Velocity Blood Flow: Limitations Due to Clutter Signals from Vibrating Muscles". Andreas Heimdal IEEE Transactions on Ultrasonics, Ferroelectrics, and Frequency Control, vol. 44, No. 4, Jul. 1997.
Levine, Ruth; "Pharmacology: Drug Actions and Reactions"; 6th Edition, Parthenon Publishing, New York, 2000, pp. 102-105.

* cited by examiner

*Primary Examiner*—Elli Peselev
(74) *Attorney, Agent, or Firm*—Norris, McLaughlin & Marcus, P.A.

(57) ABSTRACT

The invention relates to an intravenous pharmaceutical form of administration including undissolved active ingredient parts, and to a kit containing the constituents for producing one such form of administration.

12 Claims, 1 Drawing Sheet

INTRAVENOUS PHARMACEUTICAL FORM OF ADMINISTRATION

This application is a continuation of international application number PCT/EP2003/008421 filed Jul. 30, 2003, status pending, and which claims priority to German Patent Application DE 102 34 784.0 filed Jul. 30, 2002.

BACKGROUND OF THE INVENTION

1. Field of the Invention

The present invention relates to an intravenously administrable pharmaceutical dosage form and to a kit containing the components for the production of such a dosage form.

2. Brief Description of Related Developments

In many cases, parenteral administration of an active ingredient is the only way of achieving satisfactory treatment of a patient with a pharmaceutical active ingredient. This is, for example, the case if, due to his/her physical impairment, the patient is incapable or is capable only with difficulty of taking the active ingredient orally, the active ingredient is only inadequately resorbed via the intestinal tract or if the active ingredient is not sufficiently resistant to gastric acid or the enzymes of the digestive tract. Parenteral administration of an active ingredient is furthermore also advantageous if rapid, direct action of the active ingredient is to be achieved.

One particular form of parenteral administration is intravenous administration, in which the active ingredient is administered by means of an injection or infusion into a vein of the patient. While in the case of intravenous injection, the entire quantity of active ingredient is available in the body immediately after administration, intravenous infusion makes it possible to administer the entire quantity of active ingredient over a longer period of time.

Pharmaceutical active ingredients are administered intravenously virtually exclusively by means of an aqueous solution of the particular active ingredient, as miscibility of the administered solution with the patient's blood is an essential prerequisite for safe administration. If this miscibility is not present, the patient runs the risk of life-threatening embolisms or severe necrosis which may even entail amputation of the corresponding limb. While intravenously administrable oil-in-water emulsions comprising a lipophilic active ingredient in the disperse phase are known, the capacity of such emulsions to absorb the lipophilic active ingredient is restricted, on the one hand, by the solubility of the active ingredient in the oil phase and, on the other, by the physical stability of the emulsion, such that this mode of administration has not become widespread.

Intravenous administration of active ingredients is thus conventionally limited to those active ingredients which are characterised by sufficient water solubility. This ensures that a quantity of the active ingredient which is necessary for satisfactory treatment of the patient may be completely dissolved in the aqueous medium to be administered. Numerous active ingredients with poor to very poor water solubility, on the other hand, may conventionally only be administered to the patient by other routes, for example orally or rectally, as the volume of the aqueous medium which would be required completely to dissolve the active ingredient is such that intravenous administration is no longer possible. One of the disadvantages of oral or rectal administration is that larger quantities of active ingredient must generally be administered than would be required for satisfactory patient treatment in the case of intravenous administration of the particular active ingredient. Where active ingredients with poor water solubility are nevertheless used in a volume conventional for intravenous administration which results in an insoluble fraction, only an average particle size in the nanometre range of the undissolved fraction of the active ingredient would be permissible and tolerable because such particles are immediately soluble on administration. However, converting the active ingredient into particles in the nanometre range is complex and costly.

SUMMARY OF THE INVENTION

The object underlying the present invention was accordingly to provide an intravenously administrable pharmaceutical dosage form also for an active ingredient with unsatisfactory water solubility, which dosage form contains a sufficient quantity of active ingredient for satisfactory patient treatment and whose water-insoluble active ingredient fraction may not only comprise particles in the nanometre range in order, inter alia, to avoid elaborate preparation of the active ingredients.

This object is achieved according to the invention by the provision of an intravenously administrable pharmaceutical dosage form which comprises one or more pharmaceutical active ingredients which are in each case at least partially undissolved in a water-based suspending medium and this undissolved active ingredient fraction has an average particle size of $\geq 5$ μm, wherein of these the fraction of particles with a particle size in the range from greater than 2 μm–100 μm amounts to at least 80% of the total mass of the particles and this undissolved active ingredient fraction is at most of such a size that, when diluted with up to 500 ml of phosphate buffer solution at body temperature, preferably $\geq 35°$ C., it dissolves within a predetermined administration time.

The average particle size of the undissolved active ingredient particles is preferably in the range from >5 μm to 35 μm, wherein of these the fraction of particles with a particle size in the range from 3-80 μm, preferably from 3-50 μm, preferably amounts to at least 80% of the total mass the particles.

The intravenously administrable pharmaceutical dosage form according to the present invention is suitable for the administration of pharmaceutical active ingredients both to humans and to animals. It is preferably suitable for the administration of pharmaceutical active ingredients to humans.

Apart from the slight natural variation between individual members of a species, body temperature also varies for example as a function of the, for example human or animal, species which is to be treated in each case, or as a function of the particular condition, such as for example hypothermia or fever.

The person skilled in the art is familiar with the corresponding temperature ranges which must be taken into consideration for the particular species, in particular for humans. The corresponding temperature is preferably the specific body temperature of the person to be treated, particularly preferably $\geq 35°$ C.

The administration time substantially depends on the solubility characteristics of the undissolved active ingredient fraction in the predetermined volume of phosphate buffer solution and the place of administration, for example the arm. Suitable methods for determining the necessary administration time as a function of the place of administration are known per se to the person skilled in the art and are described, for example, in "Physiologie des Menschen" [human physiology] by R. F. Schmidt, G. Thews, Springer Verlag Berlin, Heidelberg, New York, 20th edition 1980. The corresponding literature description is hereby introduced as a reference and is deemed to be part of the disclosure.

The administration time necessary for the particular dosage form according to the invention may be determined by the person skilled in the art by simple preliminary testing with the assistance of a measurement in the model described below, wherein, in order to eliminate any risk to health, the administration time determined in this manner should be extended by at least 10% to at most 100%.

Administration time is determined by first of all determining the necessary solubility of the undissolved active ingredient fraction with the assistance of a standard phosphate buffer solution with a pH value of 7.413 (at 25° C.). The pH value of this standard buffer solution at a temperature of 37° C. may be determined using conventional methods known to the person skilled in the art. The corresponding standard buffer solution is commercially obtainable, for example from Riedel-de Haen, Hanover, Germany.

The intravenously administrable dosage form according to the invention may assume the form both of an injection and of an infusion. The intravenously administrable dosage form according to the invention preferably assumes the form of an injection.

The suspension volume of the intravenously administrable dosage form according to the invention should be of the order of magnitude conventional for this type of dosage and known to the person skilled in the art, provided that the above-stated conditions according to the invention are satisfied.

Provided that the dosage form according to the invention is intended for intravenous administration by injection, the suspension volume is preferably 0.1 to 15 ml, particularly preferably 0.5 to 10 ml.

If the dosage form according to the invention is intended for intravenous administration by infusion, the volume of the intravenously administrable suspension is preferably >15 to 500 ml, particularly preferably 50 to 250 ml.

In the dosage form according to the invention, the fraction of undissolved active ingredient particles in the suspension to be administered intravenously has an average particle size of >5 µm, preferably in the range from >5 to 35 µm, wherein the fraction of particles with a particle size in the range from >2 µm–100 µm, preferably in the range from 3-80 µm, particularly preferably in the range from 3-50 µm, amounts to at least 80% of the total mass of these active ingredient particles. These particle sizes of the undissolved active ingredient particles are determined by means of laser diffraction measurement in a Coulter® LS 230 laser particle analyser with HFM and MVM module (Beckman-Coulter Electronics GmbH, Krefeld, Germany) by particle volume evaluation.

The suspending medium used to measure the particular particle sizes is an isotonic sodium chloride solution with the addition of 0.1 wt. % polysorbate 80, in which the active ingredient in powder form is suspended by shaking. The measurement is made immediately after suspension.

The intravenously administrable dosage form according to the invention may comprise one or more pharmaceutical active ingredients, provided that they satisfy the above-stated conditions. The intravenously administrable dosage form according to the invention preferably contains in each case only one pharmaceutical active ingredient, the dose of which to be administered is present in at least partially undissolved, preferably suspended, form in the administration volume.

The intravenously administrable dosage form according to the invention may contain as pharmaceutical active ingredients any pharmaceutical active ingredient which satisfies the above-stated conditions, i.e. which, while not being completely soluble in the volume to be administered comprising the active ingredient dose to be given, does dissolve, preferably in molecularly disperse form, within the administration time on dilution with up to 500 ml of the stated phosphate buffer solution at body temperature without the undissolved particles necessarily having an average particle size in the nanometre range. The dosage form according to the invention is here in particular suitable for active ingredients which are moderately to sparingly soluble in water. The dosage form according to the invention preferably contains one or more active ingredients selected from the group consisting of analgesics, antiadipose agents, analeptics, antihypoxaemic agents, antirheumatics, opioid antagonists, anthelmintics, antiallergics, antiarrhythmics, antibiotics, antidementia agents (nootropics), antidiabetic agents, antiemetics, antivertigo agents, antiepileptics, antihypertensives, antihypotensives, antimycotics, antiinflammatory agents, antitussives, expectorants, antiarteriosclerotics, β-receptor blockers, calcium channel blockers, broncholytics, antiasthma agents. cholinergics, diuretics, circulation-promoting agents, antiaddiction agents, geriatric agents, hypnotics, sedatives, immunomodulators, oral therapeutic agents, pharyngeal therapeutic agents, coronary agents, lipid-reducing agents, local anaesthetics, neural therapeutic agents, gastric agents, intestinal agents, migraine agents, muscle relaxants, narcotics, neuropathy preparations, ophthalmic agents, otological agents, antiparkinson agents, psychopharmaceuticals, rhinological agents, sinusitis agents, spasmolytics, thrombocyte aggregation inhibitors, antituberculosis agents, urological and cytostatic agents.

The pharmaceutical active ingredient is particularly preferably selected from the group consisting of analgesics, analeptics, antihypoxaemic agents, antiallergics, antiarrhythmics, antiemetics, antivertigo agents, antihypertensives, antihypotensives, antitussives, expectorants, β-receptor blockers, calcium channel blockers, ophthalmic agents, otological agents, spasmolytic and urological agents, very particularly preferably from the group of analgesics, such as for example paracetamol.

The intravenously administrable dosage form according to the invention may also contain the particular active ingredient(s) in the form of a corresponding physiologically acceptable compound, preferably in the form of a corresponding physiologically acceptable salt or solvate compound, providing that this compound satisfies the above-stated conditions. The active ingredient is converted into powder form for preparation of the dosage form according to the invention.

The intravenously administrable dosage form according to the invention contains water or a water-based medium as the liquid suspending medium.

Apart from water, the suspending medium may here also contain conventional physiologically acceptable auxiliary substances known to the person skilled in the art. These physiologically acceptable auxiliary substances are preferably selected from the group consisting of pH-regulators, regulators for adjusting osmolality, surface-active compounds, viscosity regulators, peptising agents, buffers and preservatives.

Apart from one or more representatives of one class of auxiliary substances, the suspending medium may also contain one or more representatives of one to all of the other stated classes of auxiliary substances.

If the intravenously administrable dosage form according to the invention contains physiologically acceptable surface-active compounds, the latter are preferably polyalkylene glycols, such as for example polyethylene glycols, polypropylene glycols or ethylene oxide/propylene oxide block copolymers, phospholipids, ethers or esters of saturated or unsaturated fatty alcohols or fatty acids with polyalkylene glycols, such as for example polyethylene glycols or polypropylene glycols, polysorbates, such as mono-, di-, or triesters of saturated or unsaturated fatty acids, preferably oleic acid, lauric acid, palmitic acid or stearic acid, and sorbitol and/or the anhydride thereof, which may comprise up to 20 mol of ethylene oxide units per mol of sorbitol or sorbitol anhydride, preferably polyethoxysorbitan monolaurate with 20 ethylene oxide units, polyethoxysorbitan monolaurate with 4 ethylene oxide units, polyethoxysorbitan monopalmitate with 20 ethylene oxide units, polyethoxysorbitan monostearate with 20 ethylene oxide units, polyethoxysorbitan monostearate with 4 ethylene oxide units, polyethoxysorbitan tristearate with 20 ethylene oxide units, polyethoxysorbitan monooleate with 20 ethylene oxide units, polyethoxysorbitan monooleate with 5 ethylene oxide units or polyethoxysorbitan trioleate with 20 ethylene oxide units. A mixture of at least two representatives from different, above-stated classes of surface-active compounds or of at least two representatives from one class of surface-active compounds may also be used.

Numerous corresponding polysorbates are offered for sale under the trade name Tween® by ICI Surfactants (Essen, Germany).

In order to minimise or completely rule out the risk of cell and tissue damage on intravenous administration of the dosage form according to the invention, the osmolality, i.e. the tonicity of the dosage form according to the invention is preferably adjusted such that it is isotonic or at least approximately isotonic to physiological osmolality. The osmolality of the intravenously administrable dosage form according to the invention is thus preferably adjusted such that it is in the range from 250 to 400 mOsm/kg, particularly preferably in the range from 260 to 320 mOsm/kg and very particularly preferably in the range from 280 to 300 mOsm/kg.

Preferred regulators for adjusting osmolality are water-soluble, physiologically acceptable compounds such as inorganic salts, for example alkali metal salts, preferably sodium chloride, sugars, for example sucrose or dextrose, sugar alcohols, for example mannitol, or polyalkylene glycols, for example polyethylene glycols, preferably those with a molecular weight of 1000 to 8000 g/mol. A mixture of at least two representatives from different, above-stated classes of regulators or at least two representatives from one class of regulators may also be used to adjust osmolality.

An auxiliary substance may optionally also be used to adjust different properties of the intravenously administrable dosage form according to the invention. A surface-active compound may, for example, also serve to adjust osmolality.

The pH value of the intravenously administrable dosage form according to the invention should preferably be in the range from pH 5 to pH 8 in order to minimise or completely rule out the risk of cell and tissue damage. The pH value of the dosage form according to the invention may be adjusted using conventional methods known to the person skilled in the art.

The intravenously administrable dosage form according to the invention may also contain physiologically acceptable preservatives. Suitable substances of this kind are, for example, 1,1,1-trichloro-2-methyl-2-propanol, phenylethyl alcohol, sorbic acid, benzyl alcohol, alkylbenzyl dimethylammonium chloride with a chain length of $C_8$ to $C_{18}$ in the alkyl moiety, m-cresol or 4-hydroxyalkyl benzoate, preferably 4-hydroxymethyl benzoate or 4-hydroxypropyl benzoate. Mixtures of two or more of the above-stated physiologically acceptable preservatives may also be used.

The present invention also provides a kit for the production of the intravenously administrable dosage form according to the invention, which kit contains the components necessary for the production of said dosage form at least partially separate from one another.

In a preferred embodiment, this kit consists of two vessels, wherein one vessel contains the suspending medium and the other vessel the pharmaceutical active ingredients(s), preferably in powder form.

According to a preferred embodiment, at least one of these vessels may be an ampoule or bottle (vial), wherein one vessel may preferably be docked to the other for mixing.

In a further preferred embodiment, the kit assumes the form of a two-chamber syringe, wherein one chamber contains the suspending medium and the other chamber the active ingredient particles to be suspended.

Provided that the above-stated conditions are met, the quantity of the particular active ingredient or of the particular compound of said active ingredient to be administered in each case to the patient in the intravenously administrable dosage form according to the invention may vary, for example as a function of patient weight and the nature of the condition or disease to be treated. On the basis of the properties of the particular active ingredients, the person skilled in the art knows the dosages in which the latter are to be used in order to achieve the desired therapeutic effect.

The intravenously administrable dosage form according to the invention or the components thereof may be produced using conventional methods known to the person skilled in the art. Where the intravenously administrable dosage form according to the invention is formulated in ready-to-administer form, production may preferably proceed using the method described below.

Where solid physiologically acceptable auxiliary substances are used, they are dissolved at room temperature, approx. 15 to 25° C., or optionally with heating in water for injection. If the auxiliary substances are liquid, they are mixed with the water. The resultant solution or mixture is then sterile filtered using a filter which retains microorganisms. The pore size of the filter is conventionally 0.2 µm. Filtration may optionally proceed before the physiologically acceptable auxiliary substances are added, but in this case further production of the dosage form according to the invention should proceed under aseptic conditions.

The sterile pharmaceutical active ingredient powder is then introduced under aseptic conditions through tubes into the suspending medium obtained and the resultant suspension is then packaged into suitable containers, preferably injection bottles (vials) or infusion bottles.

Where production of the intravenously administrable dosage form according to the invention has not already been performed under aseptic conditions, final sterilisation may optionally be performed in accordance with conventional methods known to the person skilled in the art, for example by autoclaving. Preferably, however, the intravenously administrable dosage form according to the invention has already been produced under aseptic conditions.

By means of the intravenously administrable pharmaceutical dosage form according to the invention, it is possible to administer preferably pharmaceutical active ingredients with poor to very poor water solubility intravenously in a dose sufficient for the necessary treatment of the patient, without its being necessary to subject the active ingredient to elaborate treatment in order to obtain a particle size in the nanometre range.

Furthermore, pharmaceutical active ingredients with good water solubility may be administered intravenously in a smaller administration volume, which in particular in the case of infusions inter alia has the advantage that the risks arising on administration of large volumes, for example pulmonary oedema, can be eliminated or at least reduced.

The osmolality of the intravenously administrable dosage form according to the invention is determined by freezing point depression according to Pharm. Eur. 97, Chapter 2.2.35. The corresponding literature description is hereby introduced as a reference and is deemed to be part of the disclosure. Measurement was performed with a type M measuring instrument (Dr. H. Knauer K G, Berlin, Germany). Calibration was performed with distilled water for 0 mosmol/kg and with a calibrating solution (Dr. H. Knauer KG, Berlin, Germany) or alternatively 12.687 g of sodium chloride dissolved in 1 kg of distilled water for 400 mOsmol/kg.

Phosphate buffer solution with a pH value of 7.413 (at 25° C.) is produced by drying potassium dihydrogenphosphate and disodium hydrogenphosphate for 2 hours at 110-130° C. before weighing out and cooling them in the desiccator. 1.179 g of potassium dihydrogenphosphate and 4.30 g of disodium hydrogenphosphate are then dissolved in approx. 800 ml of water and packaged at 25° C. in 1000 ml portions.

BRIEF DESCRIPTION OF THE DRAWING

Determination of the dissolution behaviour of the undissolved active ingredient fraction using a circulation model:

The circulation model is shown in FIG. 1.

Figure 1:
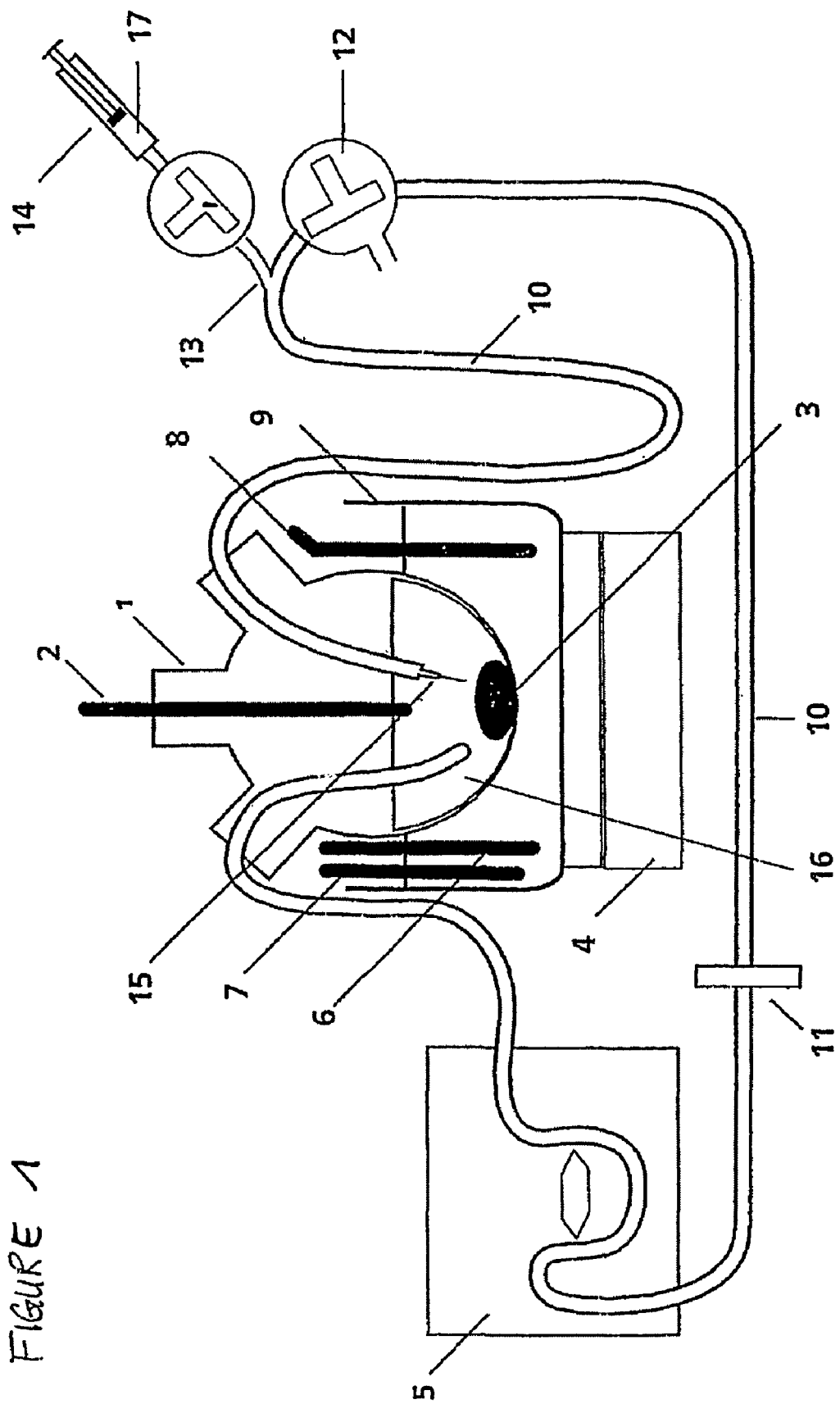

This circulation model is an in vitro simulation of the human circulatory system with blood vessels, heart and lung. The test medium used was phosphate buffer solution with a pH value of 7.413 (at 25° C.) of the above-stated composition.

The 500 ml three-necked flask (1) contains 200 ml of the above-described phosphate buffer solution (16) as the test medium. This three-necked flask simulates the heart. The three-necked flask is located in a temperature-controlled tank (9), the temperature of which is adjusted to 37° C. The inflow (7) and outflow (8) of the temperature-control liquid into and out of the temperature-controlled bath maintain the temperature throughout the entire investigation at a constant 37° C. The temperature of the temperature-control liquid is monitored and controlled with the assistance of the temperature sensor (6), while the temperature of the test medium is monitored and controlled with the temperature sensor (2). The test medium in the three-necked flask is stirred with a magnetic stirring bar (3) and magnetic stirrer (4). An infusion tube (10) is immersed in the test medium in the three-necked flask and is guided through a side opening of the three-necked flask to a peristaltic pump (5). The peristaltic pump (5) causes the test medium to flow within the infusion tube system (10) and back to the three-necked flask. Downstream from the peristaltic pump (5), a particle filter (11) with a pore size of 0.2 µm is inserted in the infusion tube system (10), this filter simulating the lung. Downstream from the particle filter (11), the infusion tube (10) leads to a three-way tap (12) and thence to a Y-piece (13). On one side of the Y-piece, the infusion tube continues onwards and through the second side opening in the three-necked flask, so completing the circulatory system. The infusion tube comes to an end under the liquid level with a cannula (15). A three-way tap and a syringe (14) is connected to the other side of the Y-piece. The syringe contains the intravenous dosage form (17) to be tested.

When the three-way tap to the syringe is closed, the test medium is pumped from the three-necked flask by means of the peristaltic pump through the infusion tube system and the filter back to the three-necked flask. While the intravenous suspension is being injected, the three-way tap to the syringe is opened and the suspension injected with the syringe. After injection, the three-way tap to the syringe is closed again. The speed of administration and the resultant administration time for a determined volume is established by ensuring that, at the latest on entry into the test medium, any turbidity due to insoluble fractions has disappeared. Complete dissolution is also verified by inspection of the particle filter (11).

The invention is explained below with reference to Examples. These explanations are given merely by way of example and do not restrict the general concept of the invention.

EXAMPLES

Example 1

Intravenously Administrable Suspension of Paracetamol

Paracetamol powder with a particle size of approx. 98 wt. % smaller than 50 µm and approx. 80 wt. % smaller than 10 µm was packaged in 1.0 g portions in vials made from (15R) tube glass, closed with a pierceable-septum bung of bromobutyl rubber and sealed with a crimped cap.

1 g of paracetamol was suspended using 5 ml of isotonic sodium chloride solution with the addition of 0.1 vol. % of polysorbate 80 (mixture of sorbitol partial esters with oleic acid and sorbitol and/or the anhydride thereof with in each case up to 20 mol of ethylene oxide per mol of sorbitol and/or sorbitol anhydride). The particle size of this suspension was determined immediately after the production thereof using the above-stated method. The average particle size of the undissolved particles was >5 µm, wherein the fraction of particles with a particle size in the range from 6-40 µm was 80%.

Example 2

Intravenously Administrable Suspension of Paracetamol

Paracetamol with a particle diameter of approx. 98 wt. % smaller than 50 µm and approx. 80 wt. % smaller than 10 µm was packaged in 1.0 g portions in vials made from (15R) tube glass, closed with a pierceable-septum bung of bromobutyl rubber and sealed with a crimped cap. 1 g of paracetamol powder was suspended using 10 ml of isotonic sodium chloride solution with the addition of 0.1 wt. % of polysorbate 80, a mixture of sorbitol partial esters and the anhydrides thereof with oleic acid, copolymer with approx. 20 mol of ethylene oxide for each mol of sorbitol and sorbitol anhydride.

Testing of the dissolution of the undissolved fraction was performed using the above-described circulatory model. On injection of each of the suspensions according to the invention of Examples 1 and 2, the paracetamol dissolved in the infusion tube to the three-necked flask and in the three-necked flask. The test liquid leaving the three-necked flask contained no undissolved constituents. Recirculation of the model liquid was possible at all times. No clogging of the 0.2 µm particle filter (11) and thus blocking of the circulatory system occurred.

The invention claimed is:

1. A method of administering a pharmaceutically active compound to a patient in need thereof comprising intravenously administering a therapeutically effective amount of the active compound to the patient in the form of a dosage form, said dosage form comprising a combination of (a) undissolved particles consisting of one or more pharmaceutical active compounds suspended in (b) a water-based suspending medium, wherein (i) the undissolved particles have an average particle size of ≧5 μm.
(ii) at least 80% of the total mass of undissolved particles is made up of undissolved particles having a particle size ranging from >2 μm up to 100 μm,
(iii) the dosage form is in a form suitable for intravenous administration, and
(iv) the dosage form exhibits the property that when the dosage form is intravenously administered to a patient then any undissolved particle entering the patient's body dissolves during a period of time, wherein that period of time is defined as the time required for said particle to travel intravenously from a first point to a second point within the patient's body, wherein the first point is defined as the point at which said particle is intravenously introduced into the patient's bloodstream, and the second point is defined as the point at which said particle, traveling in the patient's bloodstream, first exits from the patient's heart.

2. The method of claim 1, which comprises intravenously injecting the patient with the dosage form.

3. The method of claim 1, which comprises intravenously infusing the patient with the dosage form.

4. The method according to claim 1, where
the undissolved particles of the active compound have an average particle size in the range from >5 μm to 35 μm, and
at least 80% of the total mass of the undissolved particles of the active compound are particles with a particle size in the range from 3 to 80 μm.

5. The method according to claim 1, wherein the active compound particles are suspended in the suspending medium.

6. The method according to claim 1, wherein the pharmaceutical active compound is at least one active compound which is selected from the group consisting of analgesics, antiadipose agents, analeptics, antihypoxaemic agents, antirheumatics, opioid antagonists, anthelmintics, antiallergics, antiarrhythmics, antibiotics, antidementia agents (nootropics), antidiabetic agents, antiemetics, antivertigo agents, antiepileptics, antihypertensives, antihypotensives, antimycotics, antiinflammatory agents, antitussives, expectorants, antiarteriosclerotics, n-receptor blockers, calcium channel blockers, broncholytics, antiasthma agents, cholinergics, diuretics, circulation-promoting agents, antiaddiction agents, geriatric agents, hypnotics, sedatives, immunomodulators, oral therapeutic agents, pharyngeal therapeutic agents, coronary agents, lipid-reducing agents, local anaesthetics, neural therapeutic agents, gastric agents, intestinal agents, migraine agents, muscle relaxants, narcotics, neuropathy preparations, ophthalmic agents, otological agents, antiparkinson agents, psychopharmaceuticals, rhinological agents, sinusitis agents, spasmolytics, thrombocyte aggregation inhibitors, antituberculosis agents, urological and cytostatic agents.

7. The method according to claim 6, wherein the pharmaceutical active compound is selected from the group consisting of analgesics, analeptics, antihypoxaemic agents, antiallergics, antiarrhythmics, antiemetics, antivertigo agents, antihypertensives, antihypotensives, antitussives, expectorants, β-receptor blockers, calcium channel blockers, ophthalmic agents, otological agents, spasmolytics and urological agents.

8. The method according to claim 6, wherein the pharmaceutical active compound is paracetamol.

9. The method according to claim 1, wherein the dosage form further comprises one or more physiologically acceptable auxiliary substances.

10. The method according to claim 4, where at least 80% of the total mass of the undissolved particles of the active compound are particles with a particle size in the range from 3 to 50 μm.

11. The method according to claim 7, wherein the pharmaceutical active compound is an analgesic.

12. The method according to claim 9, wherein the one or more physiologically acceptable auxiliary substances are one or more members selected from the group consisting of pH-regulators, regulators for adjusting osmolality, surface-active compounds, viscosity regulators, peptizing agents, buffers, and preservatives.

\* \* \* \* \*